(12) United States Patent
Oliviusson et al.

(10) Patent No.: US 10,578,625 B2
(45) Date of Patent: Mar. 3, 2020

(54) METHOD FOR ANALYZING POSTTRANSLATIONAL MODIFICATIONS USING GEL IEF AND MASS SPECTROMETRY

(71) Applicant: GE HEALTHCARE BIO-SCIENCES AB, Uppsala (SE)

(72) Inventors: Peter Mats Oliviusson, Uppsala (SE); Janne Lehtio, Bandhagen (SE); Rui Miguel Mamede-Branca, Solna (SE)

(73) Assignee: GE Healthcare Bio-Sciences AB, Uppsala (SE)

( * ) Notice: Subject to any disclaimer, the term of this patent is extended or adjusted under 35 U.S.C. 154(b) by 99 days.

(21) Appl. No.: 15/740,170

(22) PCT Filed: Jul. 4, 2016

(86) PCT No.: PCT/EP2016/065717
§ 371 (c)(1),
(2) Date: Dec. 27, 2017

(87) PCT Pub. No.: WO2017/005696
PCT Pub. Date: Jan. 12, 2017

(65) Prior Publication Data
US 2018/0188263 A1    Jul. 5, 2018

(30) Foreign Application Priority Data
Jul. 9, 2015 (GB) .................................. 1512012.4

(51) Int. Cl.
*G01N 27/447* (2006.01)
*G01N 33/68* (2006.01)
*C07K 1/28* (2006.01)

(52) U.S. Cl.
CPC ........... *G01N 33/6848* (2013.01); *C07K 1/28* (2013.01); *G01N 27/44795* (2013.01);
(Continued)

(58) Field of Classification Search
CPC ............................ G01N 27/44795; C07K 1/28
See application file for complete search history.

(56) References Cited

U.S. PATENT DOCUMENTS

2003/0008327 A1    1/2003  Ornatskaia
2008/0293083 A1*  11/2008  Bjellqvist .......... G01N 33/6848
                                                                    435/23

FOREIGN PATENT DOCUMENTS

WO      2003/071263 A1    8/2003
WO   WO 2007015697 A2 *  2/2007  ............ G01N 33/53

OTHER PUBLICATIONS

Maccarrone et al., "Protein Profiling and Phosphoprotein Analysis by Isoelectric Focusing," in Anton Posch(ed.), Proteomic Profiling Methods and Protocols,Methods in Molecular Biology, vol. 1295, Springer Science+Business Media New York 2015 (Year: 2015).*

(Continued)

*Primary Examiner* — Alexander S Noguerola
(74) *Attorney, Agent, or Firm* — Eversheds Sutherland (US) LLP

(57) ABSTRACT

The present invention relates to the field of proteomics and more specifically to a method for analyzing a sample possible containing peptides or modified peptides; in particular useful for biomarker discovery or validation of biomarkers. The method uses isoelectric focusing and mass spectrometry (MS) and enables identification of modified peptides with high resolution and predictability.

13 Claims, 7 Drawing Sheets

(52) U.S. Cl.
 CPC ..... *G01N 27/4473* (2013.01); *G01N 2440/00* (2013.01); *G01N 2440/14* (2013.01)

(56) References Cited

OTHER PUBLICATIONS

Philip Cohen, "The role of protein phosphorylation in human health and disease," Eur. J. Biochem. 268, 5001-5010 (2001) (Year: 2001).*

Wiltfang et al., "Consensus Paper of the WFSBP Task Force on Biological Markers of Dementia: The role of CSF and blood analysis in the early and differential diagnosis of dementia," The World Journal of Biological Psychiatry, 2005; 6(2): 69-84 (Year: 2005).*

Maccarrone et al., "Phosphopeptide enrichment by IEF," Electrophoresis 2006, 27, 4585-4595 (Year: 2006).*

PCT International Search Report and Written Opinion for PCT Application No. PCT/EP2016/065717 dated Aug. 17, 2016 (11 pages).

GB Search Report for GB Application No. 1512012.4 dated Apr. 27, 2016 (5 pages).

Beranova-Giorgianni et al., "Phosphoproteomic analysis of the human pituitary," Pituitary, 2006, 9(2):109-120.

Bjellqvist et al., "Reference points for comparisons of two-dimensional maps of proteins from different human cell types defined in a pH scale where isoelectric points correlate with polypeptide compositions," Electrophoresis, 1994, 15(3-4):529-539.

Chen et al., "Characterization of the Phosphoproteome in LNCaP Prostate Cancer Cells by In-Gel Isoelectric Focusing and Tandem Mass Spectrometry," J. Proteome Res., 2010, 9(1):174-178.

Drickamer, et al., (2006). Introduction to Glycobiology (2nd ed.). Oxford University Press, USA.

Filiou et al., "Profiling of mouse synaptosome proteome and phosphoproteome by IEF," Electrophoresis, 31(8):1294-1301.

Hung et al., "pI-based phosphopeptide enrichment combined with nanoESI-MS," Electrophoresis, 28(12):2044-2052.

Maccarrone et al., "Phosphopeptide enrichment by IEF," Electrophoresis, 2006, 27(22):4585-4595.

Millioni et al., "Pros and cons of peptide isoelectric focusing in shotgun proteomics," Journal of Chromatography A, 2013, 7:1-9.

Sigma Aldrich, 2003, "BioAnalytix" sigmaaldrich.com, [online], Available from https://www.sigmaaldrich.com/content/dam/sigmaaldrich/docs/Fluka/General_Information/fl_ analytix2.

Branca et al., "HiRIEF LC-MS Enables Deep Proteome Coverage and Unbiased Proteogenomics," Nature Methods, 2014, 11(1):59-66.

Steinau et al., "Chirurgisches Forum 2007 Fur Experimentelle and Klinische Forschung," 124 Kongress der Deutschen Gesellschaft fur Chirurgie MMunchen, 2007 (23 pages).

* cited by examiner ns with chelated titanium ions (IMAC-Ti$^{4+}$).

METHOD FOR ANALYZING POSTTRANSLATIONAL MODIFICATIONS USING GEL IEF AND MASS SPECTROMETRY

CROSS REFERENCE TO RELATED APPLICATIONS

This application claims the priority benefit of PCT/EP2016/065717 filed on Jul. 4, 2016 which claims priority benefit of Great Britain Application No. 1512012.4 filed Jul. 9, 2015. The entire contents of which are hereby incorporated by reference herein.

TECHNICAL FIELD

The present invention relates to the field of proteomics and more specifically to a method for analyzing a sample possible containing peptides or modified peptides; in particular useful for biomarker discovery or validation of biomarkers. The method uses isoelectric focusing and mass spectrometry (MS) and enables identification of modified peptides with high resolution and predictability.

BACKGROUND

The isolation and separation of biomolecules, such as proteins and peptides, has become of an increased interest during the past years. Some biomolecules need to be isolated as a last step of a biotechnological method for the production thereof, for example in the preparation of protein or peptide-based pharmaceutical compounds. Similarly there is also a need to separate biomolecules for analytical purposes in order to be able to quantify and identify the proteins and/or peptides present in a sample. A wide variety of methods are used for the detection and quantification of the separated proteins and/or peptides. For identification and characterization of separated proteins, mass spectrometry (MS) methods are commonly used as these methods are fast and require very small amounts of proteins and/or peptides.

In order to increase sensitivity in mass spectrometry methods, it is often necessary to reduce the complexity of the sample. The reason for this is that prominent proteins in a sample give rise to numerous identical peptide fragments which will be detected over and over again in the analyses, obscuring the identification of proteins/peptides in low copy numbers. There are a number of ways to achieve this; on a tissue, cell, or sub-cellular level.

A certain tissue is often isolated by excision or biopsy whereas cultured cells may be sorted into different populations by flow cytometry, e.g. through fluorescence-activated cell sorting (FACS). Cells from heterogenous tissue may also selectively be released by enzyme treatment. An example is the isolation of mesenchymal stem cells from the umbilical cord (Lechner et al., Volume 36, 2007, pp 405-406). Cells can further be fractionated into organelle fractions using density gradient ultra-centrifugation.

When proteins are extracted as a cell homogenate, its complexity can be reduced by different methods. Depletion of abundant proteins by antibodies is a common way, e.g. to remove albumin from plasma samples.

A number of chromatography methods are commonly applied to separate complex protein samples. Examples include ion-exchange chromatography where ions and polar molecules can be separated according to their affinity to the ion exchange material, separation based on hydrophobicity, affinity to metals, capture of expressed tags, e.g. his-tagged proteins, or separation by size.

Protein electrophoresis is a very common and versatile separation technology where proteins, or peptides, are separated according to their size (e.g. SDS-PAGE), intrinsic charge (e.g. isoelectric focusing, IEF), or a combination thereof (e.g. 2D-DIGE).

In SDS-PAGE, proteins are given a uniform negative charge by mixing with the anionic detergent sodium dodecyl sulfate (SDS), where the detergent will bind to proteins approximately in proportion to the protein mass. When these proteins are electrophoretically separated through a polyacrylamide gel, the separation will be based on their size only.

In isoelectric focusing (IEF), proteins are separated based on their overall intrinsic charge only, usually in an immobilized pH-gradient polyacrylamide gel. When a voltage is applied the proteins will migrate in the gradient pH-field until they reach a pH where their net charge is zero, i.e. their isoelectric point, pI.

2-dimensional electrophoresis uses IEF as the first separation method, directly followed by SDS-PAGE. This technique renders a protein map with very high resolution where also protein modifications such as phosphorylation or glycosylation can be seen. Proteins of interest are picked as small gel plugs and prepared for analyses, e.g. by MS.

Free flow electrophoresis is a similar technique to IEF, but liquid-based and continuous. A protein sample is continuously fed into a laminar buffer flow and a high voltage applied perpendicular to the flow. Separation of the sample occur based on charge density and pI, and the separated sample can be collected into different fractions. The resolution is dependent on flow speed, voltage and length of the sample cell. Arguably, the resolution is usually less good compared to IEF, where the latter can be performed in very narrow immobilized pH-ranges.

In several of the separation techniques mentioned above, apart from reducing the complexity, they may also serve as a tool to enrich certain protein populations. Partitioning of the separated sample into discrete fractions based on differences in size, hydrophobicity, pI, or buoyancy in a density gradient greatly increases the number of molecules with a specified quality. However, often molecules expressed in low copy numbers are still a problem to detect.

Selective capturing of molecules offers an advantage and has long been used in an industrial context or in research. Antibodies bound to a solid matrix, beads and/or magnetic substrates selectively capture their target antigens. Often these proteins are propagated in cells of different organisms using an expression system which give the proteins a tag that facilitates capturing. Alternatively, systems which are based on other strong protein-protein interactions are commonly used; e.g. biotin-streptavidin.

Posttranslational modifications (PTM) of proteins are very common regulators of their activity, and selectively sorting-out modified proteins from a non-modified protein population may offer means to a deeper understanding of their roles, or may be used diagnostically. There are a large number of PTMs; e.g. phosphorylation, glycosylation, alkylation, methylation, prenylation, or ubiquitination. Phosphorylation is the most studied modification and there are estimations that one third of the mammalian proteins may be phosphorylated some time in their life cycle. Capturing of phosphorylated proteins can be achieved using phospho-specific antibodies, or, more commonly, using immobilized metal affinity chromatography with chelated titanium ions (IMAC-Ti$^{4+}$).

In isoelectric focusing (IEF), the separation takes place in a pH gradient that occupies the whole separation distance and is arranged so that the pH in the gradient increases from anode towards the cathode. While other alternatives also exist, the pH gradients required in isoelectric focusing are in practice generated in two different ways: with the aid of a solution of carrier ampholytes or with an immobilized pH gradient. IEF with carrier ampholytes usually gives less good resolution as there is a pH-drift in the generated pH field, in particular when the electrophoresis proceed over long time.

In the case of an immobilized pH gradient (IPG) the charged or chargeable groups generating the pH gradient are bound either to the wall of a capillary system or to a matrix, often a polyacrylamide gel, to become convection stabilization. The immobilized charged or chargeable groups used are normally a limited number of carboxylic groups or amino groups with different pK-values distributed within or close to the pH gradient, which is to be generated. The concentration of the charged or chargeable groups is varied along the separation distance in a manner causing the pH at which the wall or the gel matrix has a zero net charge to increase from the anode to the cathode. A commercially available example of a system for generation of immobilised pH gradients is the Immobiline II System™ (Amersham Biosciences, Uppsala, Sweden), wherein a pH gradient covalently attached to a polyacrylamide gel is formed. Immobilized pH gradients are truly stationary and today they are normally used together with carrier ampholytes. In this combination the immobilized gradient determines the resulting pH gradient, while the carrier ampholytes contribute with conductivity. A common problem with isoelectric focusing of proteins and/or peptides is that the focused proteins/peptides are unevenly distributed in the gel with poor resolution.

To solve this problem for proteins, a non-linear pH-gradient has been immobilized in IEF gels, for example Immobiline DryStrips pH 3-11 NL™ (Amersham Biosciences, Uppsala, Sweden). The pH gradient is flattened in the neutral pH area where the majority of proteins have their pI. This non-linear gradient works less well for focusing of peptides. The reason for this is the uneven distribution of tryptic peptides in a broad pH field. When subjecting the whole human proteome to theoretical trypsination and using pI prediction programs optimized for peptides in urea, which is the most common solute in IEF, the peptides collect principally in three pH ranges; pH 3.4-5.0, 5.2-6.8, and pH 7.8-10 (Bjellqvist et al. Electrophoresis, 1994, 15 (3-4), 529-539). To better resolve peptides in IEF gels, a stepwise, non-linear pH gradient has been described in WO2007/073293.

IEF on Immobiline DryStrips with a linear pH gradient of pH 3.7-4.9 followed by MS has been used to reveal an unparalleled number of unique peptide identifications from human cellular samples (Branca R. M., et al. HiRIEF LC-MS enables deep proteome coverage and unbiased proteogenomics. *Nature Methods*, 2014 January; 11(1):59-62. Epub 2013 Nov. 17. PMID: 24240322).

In spite of the above there is still a need for improved methods and gels or strips for isoelectric focusing to enable reproducible isolation and enrichment of PTM peptides.

SUMMARY OF THE INVENTION

The invention relates to a novel method to separate and enrich posttranslationally modified (PTM) r peptides with both high resolution and predictability. Thus in a first aspect, the invention relates to a method for assaying a digested protein sample, comprising
a) running said sample on an isoelectric focusing gel with a pH gradient to separate peptides in said sample;
b) fractionating said gel into smaller pieces;
c) extracting peptides from the fractionated gel pieces;
d) running mass spectroscopy (MS) on the extracted peptides from selected fractions; wherein the method comprises a step of:
f) identifying peptides and any possible post translational modification (PTM) of the peptides from step d) by identifying the modification degree of the peptides, i.e. the number of modifications per peptide), and/or the position of the modification on the peptide.

Depending on the PTM to be analyzed, a defined pH-range is selected and used in combination with a focusing gel of suitable length to give sufficient resolution and fractionation into an appropriate number of fractions.

The PTM modifications are any modifications changing the pI of the peptide, such as phophorylations, glycolysations, alkylation, methylation, prenylation, or ubiquitination.

The pH-gradient comprises 0.1-1.5 pH units between pH 2-11. A preferred interval is pH 3.4-5.

In a preferred embodiment the he pH-gradient is 2.5-3.7 which is suitable for analysis of phosphorylated peptides. In this case the gel is preferably 24 cm and the number of fractions is 72. Preferably the isoelectric focusing gel is 5-40 cm in length, preferably 20-25 cm.

Preferably the protein sample is trypsin digested. In case of phosphorylated peptides the extracted peptides from step d) may be treated with alkaline phosphatase. In this way the peptides will be analyzed in their non-modified state which increases the MS detectability of those peptides.

Preferably the sample is fractionated into 15-100 fractions, preferably 72-96 fractions. 96 fractions are preferred when the peptides are extracted into a 96-well multi-plate.

Preferably the extraction of peptides in step c) is performed with a hydrophobic solute under agitation, or convection (heating).

In one embodiment all fractions are selected in step d) and analyzed further.

In a preferred embodiment of the method a subset of fractions are selected in step d) and said subset is specific for a certain disease, i.e. the PTM modified peptides in said subset are biomarkers for a certain disease. The invention enables screening in respect of presence of peptides in said subset of fractions.

The invention also relates to an isoelectric focusing gel having a pH-gradient of 2.5-3.7 and use thereof for analysis of PTM peptides.

Acidic IPG-strips used in the method according to the invention offer a unique possibility to enrich post-translationally modified peptides and to increase resolution and analytical depth in MS-analyses. Moreover, it is a bridge to clinical use as pre-defined fractions can be selected for analysis.

The experimental pI value obtained by narrow fractionation may be used to aid in identification of post-translationally modified peptides and verify/confirm peptide/protein PTM on particular peptide.

The experimental pI value obtained by narrow fractionation may also be used to localize the PTM site on peptide/protein.

DETAILED DESCRIPTION OF THE INVENTION

Figure 1:
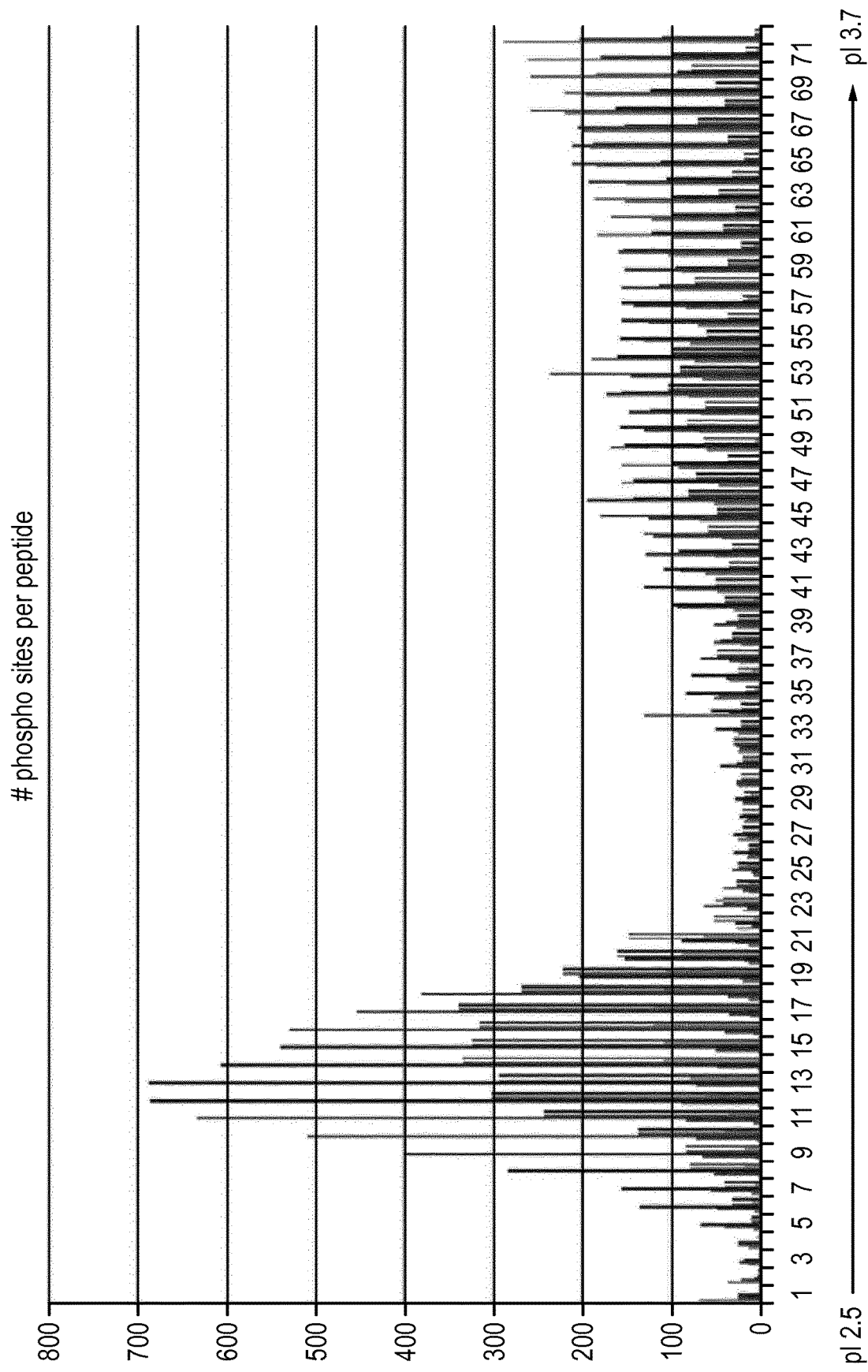
FIG. 1 is a diagram showing the distribution of the phospho-peptides, from a trypsin digested cell lysate, across the isoelectric point range.
Figure 2:
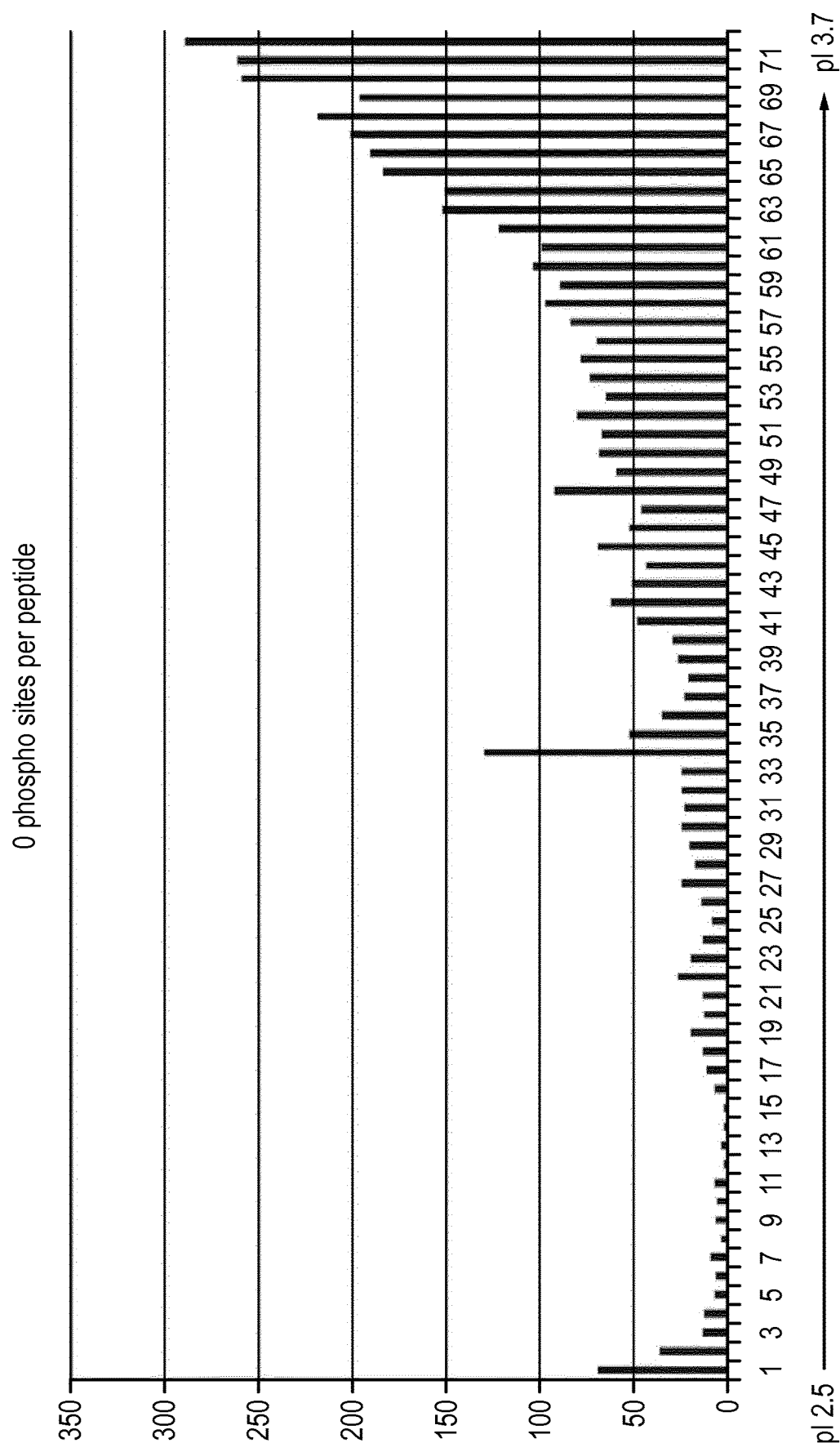
FIG. 2 is a diagram showing the distribution of non-phosphorylated peptides across the isoelectric point range.
Figure 3:
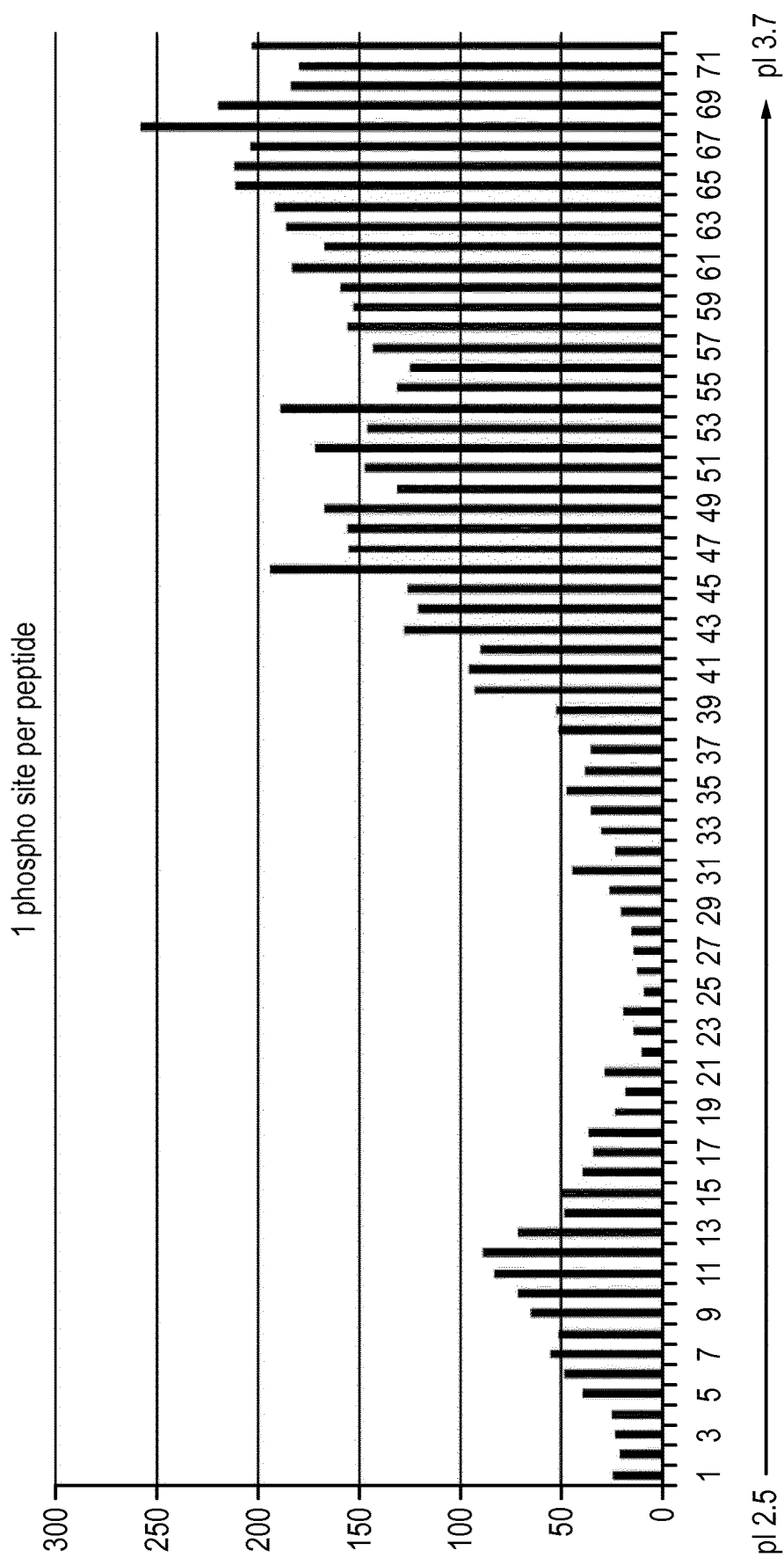
FIG. 3 is a diagram showing the distribution of singly phosphorylated peptides across the isoelectric point range.

The present invention relates to a method for isoelectric focusing electrophoresis of peptides, preferably tryptic peptides, in gel strips with an immobilized pH gradient and fractionation thereof into a number of discrete fractions. The fractions may be obtained by using a well former of similar type described in WO2006/136296 or WO 2006/136297.

Each fraction will then be used in a mass spectrometry workflow to give significantly higher concentration of peptides separated according to their pI. The method is in particular suited for MS-based selected reaction monitoring (SRM) analyses. This pre-fractionation step has proved very successful and is not dependent on antibody-based enrichment of peptides. The method is suitable for discovery proteomics or more targeted approaches in biomarker research, early validation of biomarkers, or direct clinical uses.

The uniqueness of the method is the possibility to in a highly reproducible way enrich and fractionate peptides with post-translational modifications and to separate peptides differing in single modifications, e.g. the number of phosphorylated residues.

By using highly defined pH gradients in so called gel strips, the method here described may be used to fractionate samples with very minor differences in charge, not only in the acid pH areas.

Further, the pH areas can be chosen to encompass e.g. a certain group of proteins or peptides, corresponding to their functionality, e.g. kinases, or to a group of proteins known to be involved in certain disease symptoms, e.g. inflammation or Parkinson's disease.

Bjellqvist et al. Electrophoresis, 1994, 15 (3-4), 529-539 describes three pH areas where human tryptic peptides collect (pH 3.4-5.0, 5.2-6.8, and pH 7.8-10). In-depth analyses of these three peptide populations, by the present inventors revealed that more than 90% of the human proteins could be identified from the pH area 3.4-5.0, having at least one peptide in this area. Using an immobilized pH gradient covering only this pH area would significantly reduce the sample complexity and at the same time keep the proteome coverage.

Many modifications will alter the pI of the protein/peptide as they may bind to charged amino acids and/or change their sterical conformation. For example, phosphorylation usually occurs on serine, threonine, tyrosine and histidine residues in eukaryotic proteins, where phosphorylation on serine is the most common, followed by threonine. Single phosphorylation adds a negative charge to these residues and an additional phosphorylation further increases the negative charge, i.e. their pI will be more acidic.

The present inventors realized that simultaneous MS analysis of single- or non-phosphorylated peptides together with multiple phosphorylated peptides causes a bias as the phosphate groups interfere with the ionization of the sample into the gas phase. Thus, when peptide species with diverse phosphorylation patterns are analyzed at the same time the ionisation of the multiply phosphorylated peptides is suppressed. This further emphasizes the importance of separating differently phosphorylated isoforms upstream to MS analysis.

Glycosylation is another highly common post-translational modification of proteins, which can introduce pI shifts in proteins/peptides. The residues to which the glycans bind, the sugar types of the glycans, the structure of the glycans (branched or unbranched), and the length of the glycans may all influence the pI of glycosylated peptides (Drickamer, K; M. E. Taylor (2006). Introduction to Glycobiology (2nd ed.). Oxford University Press, USA. An example of a PTM causing a significant shift in pI towards the acidic pH is the O-linked glycosylation where first the addition of N-acetylgalactosamine to serine or threonine residues occurs, followed by the addition of sialic acid.

MS analyses generally allows for the discrimination between a phosphorylated peptide and a non-phosphorylated peptide, since phosphorylation adds mass to the peptide. The present invention enables reproducible identification of a peptide with a certain pI corresponding to a certain PTM. These peptides are highly enriched in just one or a few fractions which significantly adds analytical depth to the current MS analyses, decreases analysis time and allows for targeted detection and identification e.g. validation of biomarkers. The highly reproducible pH gradient of the Immobiline DryStrips makes it also possible to treat fractionated phosphorylated samples with alkaline phosphatase to increase their MS detectability, while their phosphorylation status can still be inferred from their isoelectric point.

Moreover, this principle is not restricted to the acidic pH area but can be utilized over the whole pH spectrum. It includes evaluation of peptides changing their pI also towards more basic pH areas as a result of PTM.

The invention will now be described closer in association with the accompanying figures and some non-limiting examples.

EXAMPLES

Materials and Methods

The results in the example below are from separating 800 ug of peptides resulting from trypsin digest of whole cell lysate from the A431 human cell line.

Sample Preparation, Isoelectric Focusing and Sample Extraction

Prototype 24 cm Immobiline DryStrips pH 2.5-3.7 were rehydrated over-night in 250 ul [8M Urea, 1% (v/v) Pharmalyte 2.5-5 (GE Healthcare, art no 17-0451-01), trace amounts of Bromophenol blue]. Rehydration was made in an IPG Box (GE Healthcare, art no 28-9334-65) without oil.

Rehydrated strips were placed in a ceramic manifold (GE Healthcare, art no 80-6498-38), the manifold placed in an Ettan IPGphor 3, (GE Healthcare, art no 11-0033-64) and strips were covered in 130 ml Immobline Dry Strip Cover Fluid, PlusOne (GE Healthcare, art no 17-1335-01). Strips were connected to the electrodes with Paper wicks (GE Healthcare, art no 80-6499-33) each wetted with 175 ul water. 320 ul samples in 8M Urea and 1% (v/v) Pharmalyte 2.5-5 was loaded on the acid end of the strips using a loading bridge.

For isoelectric focusing the following parameters were set:

500 V 1 min; 4000 V 3 h; 6000 V 5 h; 10000 V 4 h; 10000 V forever.

Current limit was set to 50 uA/strip.

The isoelectric focusing proceeded until a total of 100 kVh was reached.

Immediately after the focusing was stopped, the strips were briefly rinsed in water and placed on a clean ceramic manifold. A prototype well former (described in WO2006/136296 or WO 2006/136297) was placed onto each strip to create 72 discrete fractions. Extraction of the separated peptides was made by adding Lichrosolv water, HPLC-grade (Merck, art no 1.15333.2500) into the wells using a modified Gilson 215 Liquid handler, according to the following scheme:

20 ul water was added to each well, then another 20 ul to each well, and incubated for 1 h.

20 ul was removed from each well into a micro titer 96 well plate (V-bottom, Corning #3894), then 20 ul water added into each well, and incubated for 1 h.

20 ul was removed from each well and pooled to the previous sample, then 20 ul water added as above, and incubated for 1 h.

20 ul from each well was removed and pooled to the previous sample; thus 60 ul sample was collected from each of the 72 fractions.

The micro titer plate was put in a speedvac to dry the samples over-night.

LC-MS Acquisition Method

In each LC-MS run, the LC auto sampler (HPLC 1200 system, Agilent Technologies) freshly dissolved the dry peptide mixtures in the bottom of the well using 8 µl of solvent A (see below). After mixing the liquid in the well 10×, the autosampler injected 3 µl into a C18 guard desalting column (Zorbax 300SB-C18, 5×0.3 mm, 5 µm bead size, Agilent). We then used a 15 cm long C18 picofrit column (100 µm internal diameter, 5 µm bead size, Nikkyo Technos Co., Tokyo, Japan) installed on to the nano electrospray ionization (NSI) source. Solvent A was 97% water, 3% acetonitrile (ACN), 0.1% formic acid (FA); and solvent B was 5% water, 95% ACN, 0.1% FA. At a constant flow of 0.4 µl/min, the linear gradient went from 2% B up to 40% B in 45 min, followed by a steep increase to 100% B in 5 min. Online LC-MS was performed using a hybrid LTQ-Orbitrap Velos mass spectrometer (Thermo Scientific). FTMS master scans with 30,000 resolution (and mass range 300-1700 m/z) were followed by data-dependent MS/MS (17,500 resolution) on the top 5 ions in two stages: first, using collision induced dissociation (CID) in the ion trap at 35% collision energy and ion trap MS2 acquisition; and secondly, using higher energy collision dissociation (HCD) at 20% normalized collision energy and orbitrap MS2 acquisition. Precursors were isolated with a 4 m/z window. Automatic gain control (AGC) targets were 1e6 for MS1, 2e4 for CID-ITMS2 and 5e4 for HCD-FTMS2. Maximum injection times were 100 ms for MS1, 200 ms for CID-ITMS2 and 500 ms for HCD-FTMS2. The entire duty cycle lasted ~3.5 s. Dynamic exclusion was used with 60 s duration. Precursors with unassigned charge state or charge state 1 were excluded. A precursor selection threshold of 1000 was used.

Results 5972 unique identities were detected, and 5191 thereof were phosphorylated, including peptides with up to 4 phosphorylation sites (see FIGS. 1-7).

In FIG. 1, a diagram shows the distribution of the phospho-peptides, from a trypsin digested cell lysate, across the isoelectric point range. Differentially phosphorylated peptides are found in different areas of the isoelectric point range. Peptides carrying 3 or 4 phospho-groups focus mainly in the first half of the 2.5-3.7 IPG strip and doubly phosphorylated peptides are found across the whole 2.5-3.7 range. Singly phosphorylated peptides focus in the second half of the 2.5-3.7 IPG strip. Numbers 1-71 on the x-axis denote the fractions of the wellformer tool, described above.

Figure 4:
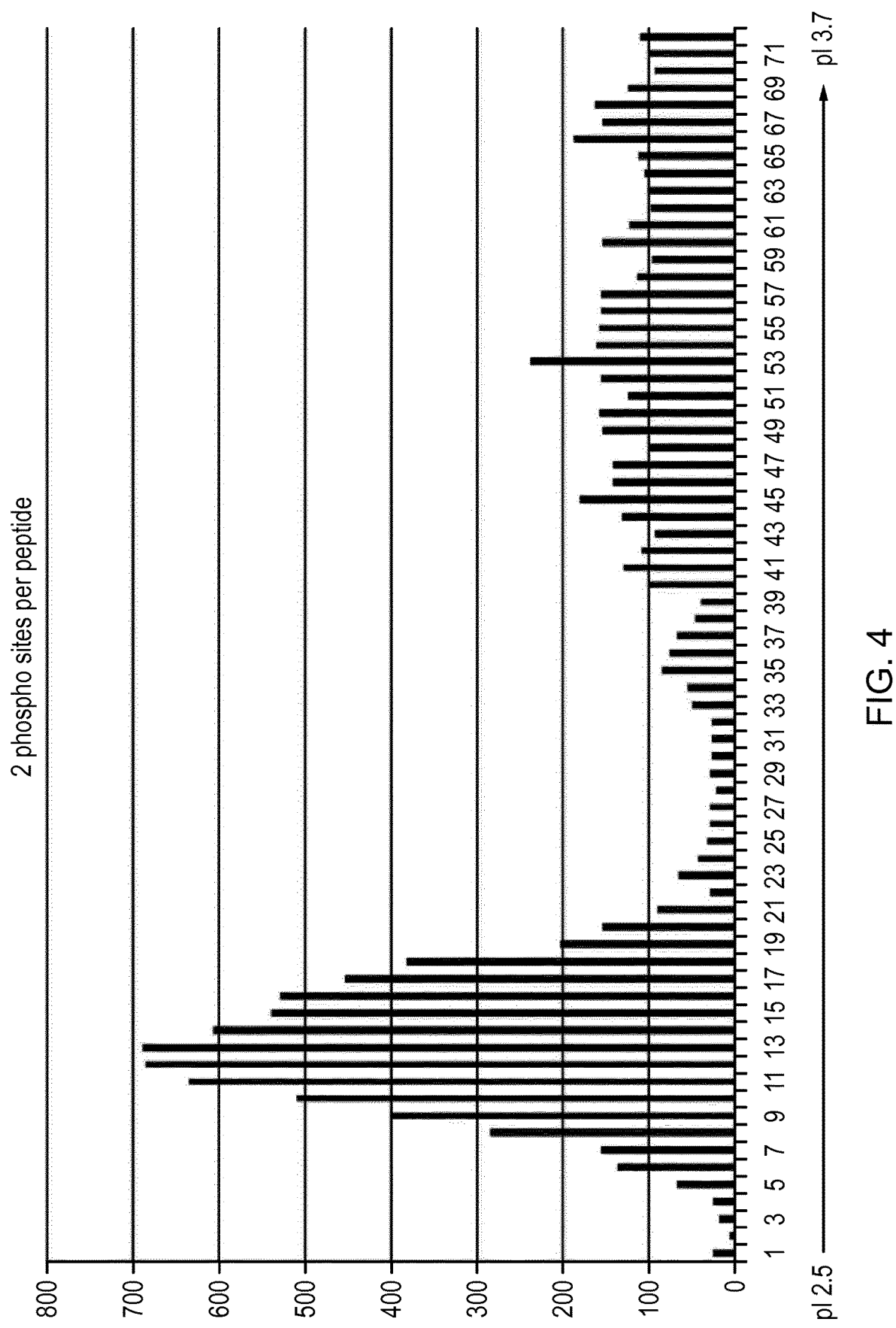
FIG. 4 is a diagram showing the distribution of peptides with two phospho-groups across the isoelectric point range.
Figure 5:
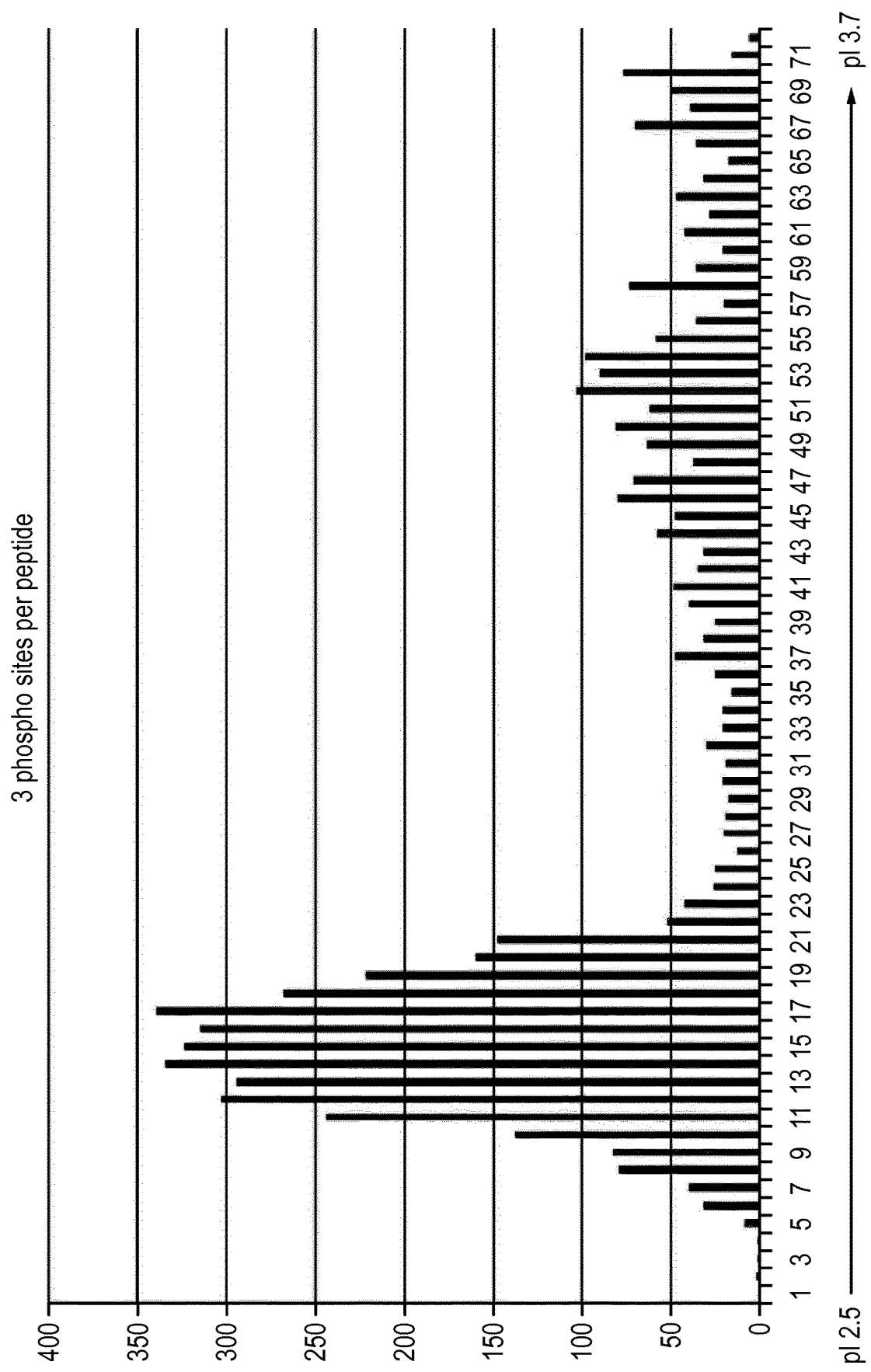
FIG. 5 is a diagram showing the distribution of peptides with three phospho-groups across the isoelectric point range.
Figure 6:
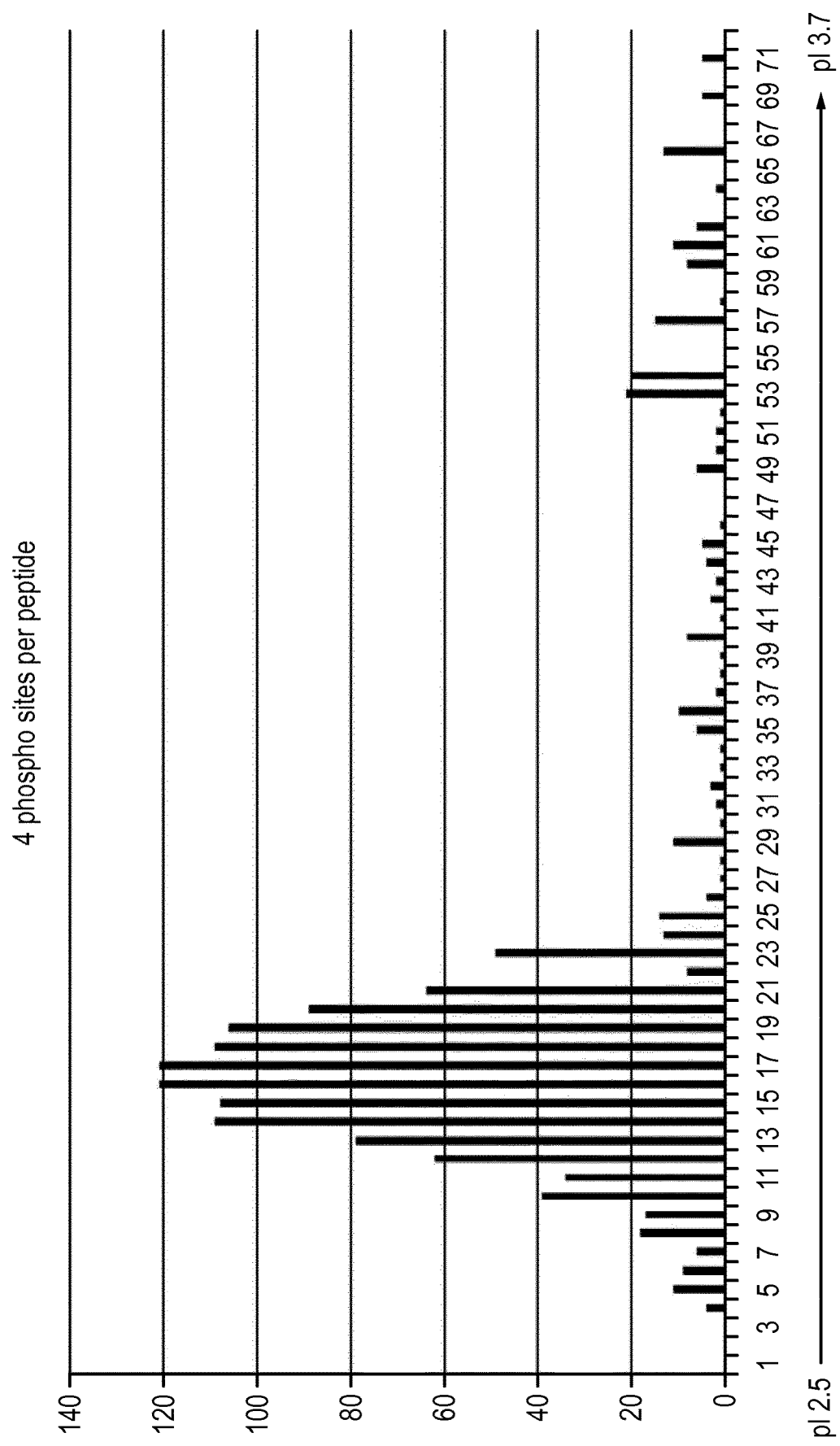
FIG. 6 is a diagram showing the distribution of peptides with four phospho-groups across the isoelectric point range.

More detailed information on how non-phosphorylated and differently phosphorylated peptides distribute across the pH range is found in FIGS. 2-6. The distribution of non-phosphorylated peptides is shown in the diagram in FIG. 2. These peptides generally collected in the less acidic area. Similarly also peptides with one phosphorylation (FIG. 3) are found towards the second half of the IPG strip. Peptides with two phosphorylations, on the other hand, collect in the acidic part of the strip (FIG. 4). This is also the case with peptides carrying three phosphorylations (FIG. 5) and four phosphorylations, as seen in FIG. 6.

A summary of the number of phosphorylated peptides identified: 2213 peptides with one phospho-site; 1915 peptides with two phospho-sites; 843 peptides with three phospho-sites; and 220 peptides with four phospho-sites.

Figure 7:
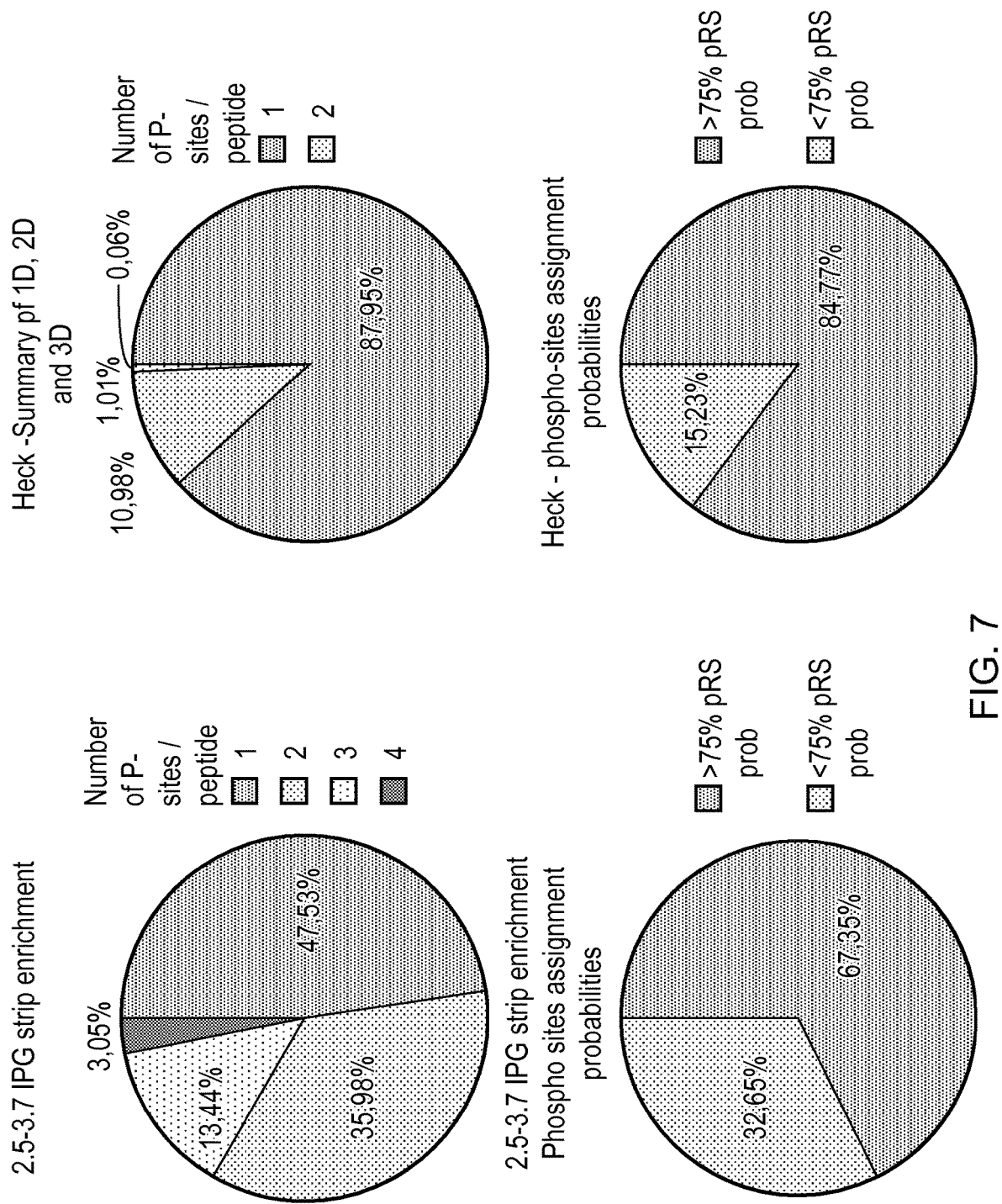
FIG. 7 shows analysis charts of number of phosphorylated peptides and phosphorylation site assignment probabilities.

The quality of the analysis and a comparison with the common IMAC-$Ti^{4+}$ method for capturing phosphorylated proteins/peptides are shown in FIG. 7. It shows analysis charts of number of phosphorylated peptides and phosphorylation site assignment probabilities. Distribution of peptides carrying single and up to four phospho-groups in a sample processed with the acidic strip method (upper left image), or with the IMAC-$Ti^{4+}$ method (upper right image) is presented. Analysis with the phosphoRS algorithm shows high probabilities for correct phospho-site assignments both for the acidic strip method (lower left image) and for the IMAC-$Ti^{4+}$ method (lower right image).

Another type of post-translationally modified peptides was also identified. Peptides with sialic acid residues added to their glycan modification were found in the Immobiline DryStrip pH 2.5-3.7. Notably, peptides with sialic acid additions were found in the Immobiline DryStrip pH 2.5-3.7 only, and not in pH 3.7-4.9 strips.

The versatility and the robustness of pH gradients cast with Immobilines makes it possible to create extremely narrow pH gradients. Besides the above prototypes, the present inventors have manufactured and used 24 cm prototype Immobiline DryStrips with a pH range of 0.25 pH units, pH 4.00-4.25. When combined with a wellformer tool of 72 wells, the resolution between sample wells is approximately 0.0035 pH units. Other examples of prototype 24 cm pH-gradient strips are 3.70-4.05, 4.20-4.45 and 4.39-4.99. These overlapping ultra-narrow pH gradient strips further increase resolution in a pH area where tryptic peptides collect.

The invention claimed is:

1. A method for assaying a digested protein sample, comprising
   a) running said sample on an isoelectric focusing gel with a pH gradient to separate peptides in said sample;
   b) fractionating said gel into smaller pieces;
   c) extracting peptides from the fractionated gel pieces;
   d) running mass spectroscopy (MS) on the extracted peptides from selected fractions; and
   e) identifying peptides and any possible post translational modification (PTM) of the peptides from step d) by identifying the modification degree of the peptides, and/or the position of the modification on the peptides, wherein the peptides comprise phosphorylated peptides, wherein extracted phosphorylated peptides from step c) are treated with alkaline phosphatase, and wherein the pH-gradient is 2.5-3.7.

2. Method according to claim 1, wherein the PTM comprises any modification changing the pI of the peptides.

3. Method according to claim 2, wherein the PTM comprises at least one of glycolysations, alkylation, methylation, prenylation, or ubiquitination.

4. Method according to claim 1, wherein the isoelectric focusing gel is 5-40 cm in length.

5. Method according to claim 1, wherein the protein sample is trypsin digested.

6. Method according to claim 1, wherein the sample is fractionated into 15-100 fractions.

7. Method according to claim 1, wherein the extraction of peptides in step c) is performed with a hydrophobic solute under agitation, or convection heating.

8. Method according to claim 1, wherein all fractions are selected in step d).

9. Method according to claim 1, wherein a subset of fractions are selected in step d) and said subset is specific for a certain disease.

10. Method according to claim 9, wherein samples from patients are screened in respect of presence of peptides in said subset of fractions.

11. Method according to claim 1, wherein identifying peptides and any possible PTM of the peptides from step d) comprises identifying the modification degree of the peptides.

12. A method comprising:

running a digested protein sample on an isoelectric focusing gel with a pH gradient to separate peptides in said sample; and identifying peptides and any possible post translational modification (PTM) of the peptides by identifying the modification degree of the peptides and/or the position of the modification on the peptides, wherein the peptides comprise phosphorylated peptides and the phosphorylated peptides are treated with alkaline phosphatase before identifying the peptides, and wherein the isoelectric focusing gel has a pH-gradient of 2.5-3.7.

13. Method according to claim 12, wherein identifying peptides and any possible PTM of the peptides comprises identifying the modification degree of the peptides.

* * * * *